United States Patent [19]

Tegeler et al.

[11] Patent Number: 5,214,059
[45] Date of Patent: May 25, 1993

[54] 2-(AMINOARYL) INDOLES AND INDOLINES AS TOPICAL ANTIINFLAMMATORY AGENTS FOR THE TREATMENT OF SKIN DISORDERS

[75] Inventors: John J. Tegeler, Bridgewater; Eileen M. Gardenhire, Califon; Grover C. Helsley, Pluckemin, all of N.J.

[73] Assignee: Hoechst-Roussel Pharmaceuticals Incorporated, Somerville, N.J.

[21] Appl. No.: 927,050

[22] Filed: Aug. 10, 1992

Related U.S. Application Data

[62] Division of Ser. No. 375,550, Jul. 3, 1989, Pat. No. 5,166,170.

[51] Int. Cl.$^5$ ............... C07D 401/04; A61K 31/44
[52] U.S. Cl. ....................................... 514/339; 546/273
[58] Field of Search ........................... 546/273; 514/339

[56] References Cited
U.S. PATENT DOCUMENTS 4,324,790 4/1982 Guillaume et al. ............... 546/273
4,410,539 10/1983 Cross et al. ...................... 546/273

*Primary Examiner*—Marianne M. Cintins
*Assistant Examiner*—Catherine S. Kilby Scalzo
*Attorney, Agent, or Firm*—Tatsuya Ikeda

[57] ABSTRACT

There are described compounds of the formula

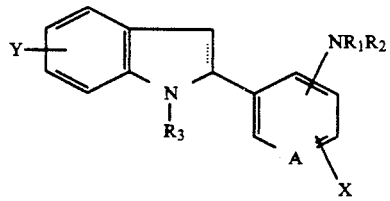

where
  A is CH or N;
  X is hydrogen, loweralkyl, halogen, trifluromethyl, loweralkoxy, arylloweralkoxy, hydroxy or phenylamino;
  Y is hydrogen, loweralkyl, halogen, loweralkoxy, arylloweralkoxy or hydroxy;
  $R_1$ is hydrogen or loweralkyl;
  $R_2$ is hydrogen, loweralkyl, formyl, alkylcarbonyl, arylloweralkylcarbonyl, arylcarbonyl, alkoxycarbonyl, arylloweralkoxycarbonyl or aryloxycarbonyl;
  $R_3$ is hydrogen, alkyl, alkylcarbonyl, arylloweralkylcarbonyl, arylcarbonyl, alkoxycarbonyl, arylloweralkoxycarbonyl, aryloxycarbonyl or —CH$_2$CO$_2$C$_2$H$_5$;

which compounds are useful as topical antiinflammatory agents for the treatment of skin disorders.

9 Claims, No Drawings

2-(AMINOARYL) INDOLES AND INDOLINES AS TOPICAL ANTIINFLAMMATORY AGENTS FOR THE TREATMENT OF SKIN DISORDERS

This is a division of a prior application, Ser. No. 375,550, filed Jul. 3, 1989, now U.S. Pat. No. 5,166,170.

The present invention relates to compounds of the formula,

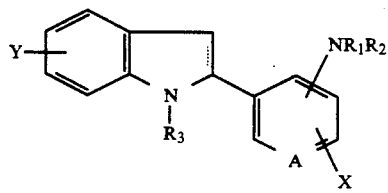

(I)

where
- A is CH or N;
- X is hydrogen, loweralkyl, halogen, trifluromethyl, loweralkoxy, arylloweralkoxy, hydroxy or phenylamino;
- Y is hydrogen, loweralkyl, halogen, loweralkoxy, arylloweralkoxy or hydroxy;
- $R_1$ is hydrogen or loweralkyl;
- $R_2$ is hydrogen, loweralkyl, formyl, alkylcarbonyl, arylloweralkylcarbonyl, arylcarbonyl, alkoxycarbonyl, arylloweralkoxycarbonyl or aryloxycarbonyl;
- $R_3$ is hydrogen, alkyl, alkylcarbonyl, arylloweralkylcarbonyl, arylcarbonyl, alkoxycarbonyl, arylloweralkoxycarbonyl, aryloxycarbonyl or $-CH_2CO_2C_2H_5$;

which compounds are useful as topical antiinflammatory agents for the treatment of various dermatoses including, for example, exogenous dermatitides (e.g. sunburn, photoallergic dermatitis, urticaria, contact dermatitis, allergic dermatitis), endogenous dermatitides (e.g. atopic dermatitis, seborrheic dermatitis, nummular dermatitis), dermatitides of unknown etiology (e.g. generalized exfoliative dermatitis), and other cutaneous disorders with an inflammatory component (e.g. psoriasis).

Unless otherwise stated or indicated, the following definitions shall apply throughout the specification and the appended claims.

The term alkyl shall mean a straight or branched alkyl group having from 1 to 22 carbon atoms. Examples of said alkyl include methyl, butyl, octyl, octadecyl, etc.

The term loweralkyl shall mean a straight or branched alkyl group having from 1 to 6 carbon atoms. Examples of said loweralkyl include methyl, ethyl, n-propyl, iso-propyl, n-butyl, iso-butyl, sec-butyl, t-butyl and straight- and branched-chain pentyl and hexyl.

The term halogen shall mean fluorine, chlorine, bromine or iodine.

The term aryl shall mean a phenyl group optionally mono-substituted with a loweralkyl, loweralkoxy, halogen or trifluoromethyl group.

The dotted line in Formula I signifies an optional double bond.

Throughout the specification and the appended claims, a given chemical formula or name shall encompass all stereo, geometrical and optical isomers where such isomers exist.

The compounds of this invention are prepared by utilizing one or more of the synthetic steps described below.

Throughout the description of the synthetic steps, the notations, A, X, Y, $R_1$, $R_2$ and $R_3$ shall have the respective meanings given above unless otherwise stated or indicated, and other notations shall have the respective meanings defined in their first appearances unless otherwise stated or indicated.

STEP A

A compound of Formula II is allowed to react with $CH_3MgHal$ where Hal is Br, Cl or I in a routine manner known to the art to afford a compound of Formula III.

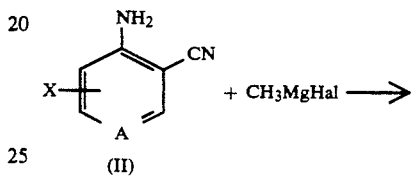

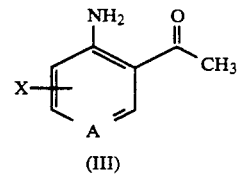

The above reaction is typically conducted in a suitable solvent such as tetrahydrofuran at a temperature of 0°-65° C. The starting compounds of Formula II where A is CH are well known, and those where A is N are disclosed in Marschik et al., U.S. Pat. No. 3,517,021.

STEP B

Compound III is allowed to react with a hydrazine of formula IV in a routine manner known to the art to afford a compound of Formula V.

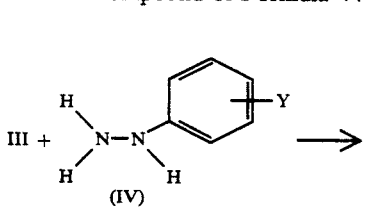

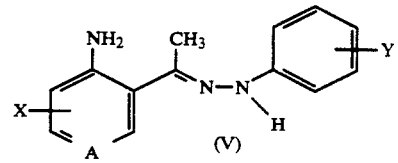

The above reaction is typically conducted in a suitable solvent such as a mixture of acetic acid and ethanol at a temperature of 20° to 80° C.

STEP C

Compound V is allowed to undergo Fischer indole synthesis reaction to afford a compound of Formula VI.

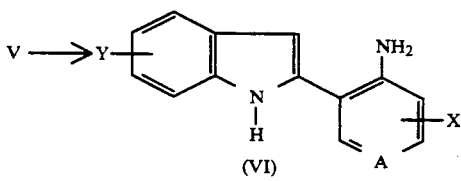

(VI)

The above reaction is typically conducted in the presence of polyphosphoric acid at a temperature of 80° to 180° C. In this reaction, if the group Y of compound V is in the ortho or para position of the phenyl ring, the cyclization reaction affords only one positional isomer, whereas if the group Y (other than hydrogen) is in the meta position, the cyclization affords two positional isomers.

Compounds of Formula VI where A is CH, Y is H and X is H, 5-chloro- or 5-bromo are disclosed in Duncan et al., J. Heterocyclic Chem., Volume 10, 65–70 (1973).

STEP D

Compound VI is allowed to react with formic acid and 1,3-dicyclohexylcarbodiimide to afford a compound of Formula VII.

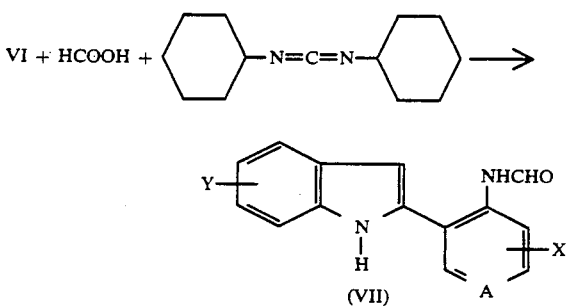

(VII)

The above reaction is typically conducted in a suitable solvent such as tetrahydrofuran at a temperature of 0° to 40° C.

STEP E

Compound VII is reduced with LiAlH$_4$ in a routine manner known to the art to afford a compound of Formula VIII.

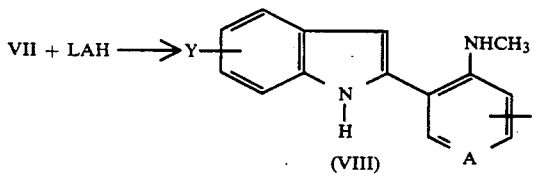

(VIII)

STEP F

Alternatively, where a compound of Formula VI, VII or VIII in which Y is hydroxy is desired, a compound of Formula VI, VII or VIII in which Y is methoxy is allowed to undergo a cleavage reaction to afford the corresponding hydroxy compound. Typically, the cleavage reaction is conducted with the aid of BBr$_3$ and a suitable solvent such as dichloromethane at a temperature of −40° to 30° C.

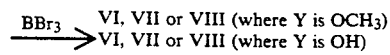

STEP G

Compound VI is reduced to afford a compound of Formula IX.

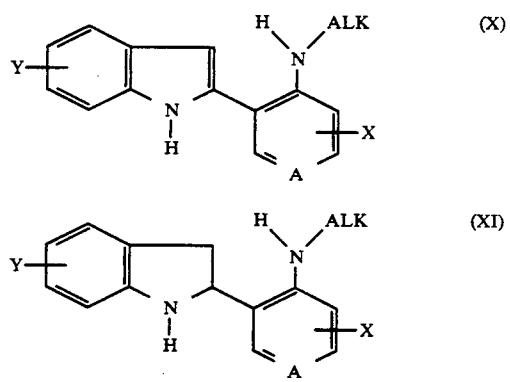

(IX)

The above reaction is typically conducted with the aid of NaCNBH$_3$ (sodium cyanoborohydride) in the presence of a suitable solvent such as acetic acid at a temperature of 0° to 30° C. Alternatively, this reaction can also be conducted with the aid of borane-tetrahydrofuran complex and trifluoroacetic acid in a suitable solvent such as tetrahydrofuran at a temperature of 0° to 30° C.

STEP H

For introducing an alkyl group into the pendent —NH$_2$ group of compound VI or VII, it is convenient to alkylate the —NH$_2$ group of compound III in a routine manner known to the art and carry out the subsequent STEPS B, C and G as described above to obtain compounds of Formula X or XI, respectively (where ALK signifies an alkyl group).

(X)

(XI)

A second alkyl group can be introduced to the pendent secondary amino group of compound X or XI in substantially the same manner as described above to afford a compound of Formula XII or XIII, respectively (where ALK' is an alkyl group which may be the same as or different from ALK).

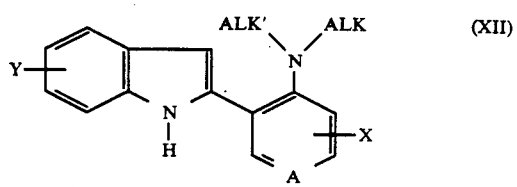

(XII)

-continued

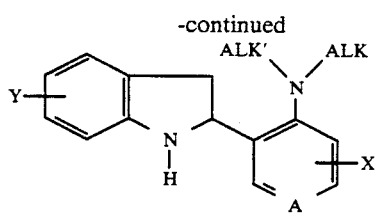 (XIII)

STEP I

A compound of Formula XIV obtained from one of the foregoing steps where $R_4$ is hydrogen, loweralkyl or formyl is allowed to react with $(CH_3)_3COC-(O)OC(CH_3)_3$ to afford a compound of Formula XV.

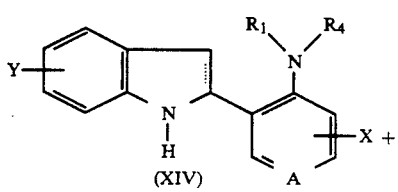

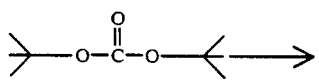

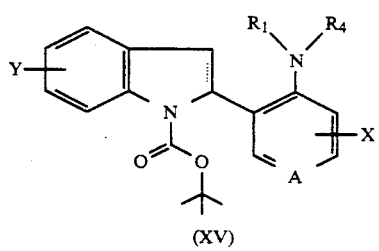

The above reaction is typically conducted in the presence of a suitable solvent such as dichloromethane at a temperature of 0° to 30° C. This STEP can be considered a special case of STEP J described below.

STEP J

For introducing an alkylcarbonyl, arylloweralkylcarbonyl, arylcarbonyl, alkoxycarbonyl, arylloweralkoxycarbonyl or arylcarbonyl group of the formula $R_5$—CO where $R_5$ is alkyl, arylloweralkyl, aryl, alkoxy, arylloweralkoxy or aryloxy, into the indole or indoline amino group of Formula XIV, assuming that one or both of $R_1$ and R is hydrogen and $R_4$ is not formyl (thus the group

can be written as

firstly, the group

is converted to

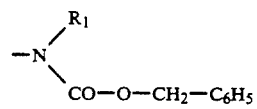

with the aid of benzyloxycarbonyl chloride or N-(benzyloxycarbonyloxy)succinimide in a routine manner known to the art, secondly, the indole or indoline amino hydrogen is replaced by —CO—$R_5$ in a routine manner know to the art, and thirdly, the resultant product is subjected to a hydrogenolysis reaction conducted in a routine manner known to the art to back convert the protected group

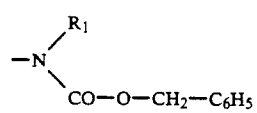

to the original group

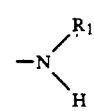

Where the group

of Formula XIV does not contain any hydrogen or already contains a formyl group, the above-described protection procedure is not necessary, but instead th substitution of the ring amino hydrogen is conducted directly. In this manner, a compound of Formula XVI is obtained.

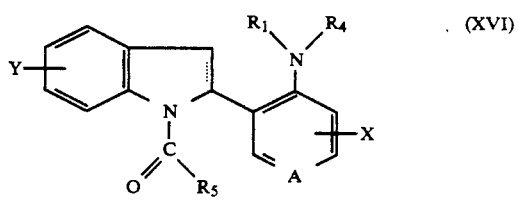 (XVI)

STEP K

Compound XIV is allowed to react with ethyl bromoacetate to replace the ring amino hydrogen with an ethoxycarbonylmethyl group to afford a compound of Formula XVII. Where necessary, the pendent amino group is protected and the protecting group is later removed in substantially the same manner as described in STEP J above.

 (XVII)

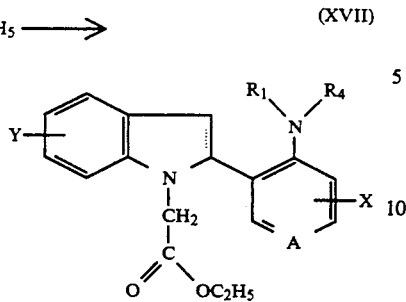

The above reaction is typically conducted in the presence of potassium carbonate, a suitable solvent such as dimethylformamide at a temperature of 5° to 80° C.

STEP L

Compound XIV is allowed to react preferably with at least two (2) equivalents of a compound of the Formula

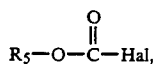

where Hal is Cl or Br to afford a compound of Formula XVIII.

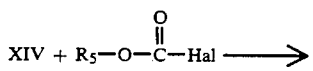 (XVIII)

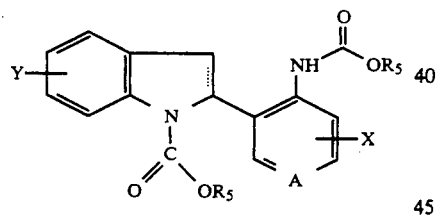

The above reaction is typically conducted in the presence of a suitable amine such as triethylamine and a suitable solvent such as dichloromethane at a temperature of 0° to 30° C.

STEP M

Compound XIV is allowed to react with about one (1) equivalent (or less) of a compound of the Formula

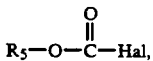

where Hal is Cl or Br to afford a compound of Formula XIX.

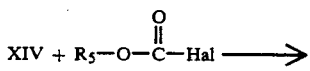 (XIX)

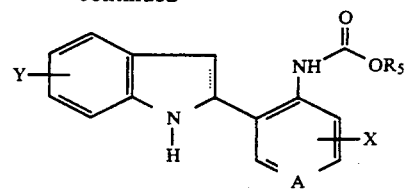

The above reaction is conducted substantially the same manner as in STEP L.

STEP N

Compound XIX is allowed to undergo a reaction step substantially the same as STEP I, J or K to afford Compound XX, XXI or XXII depicted below.

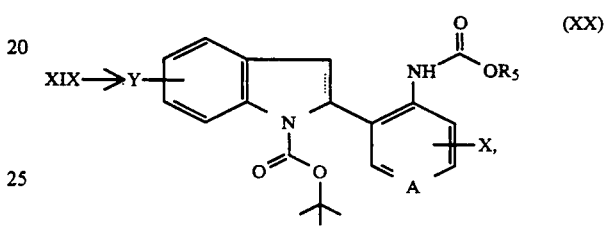 (XX)

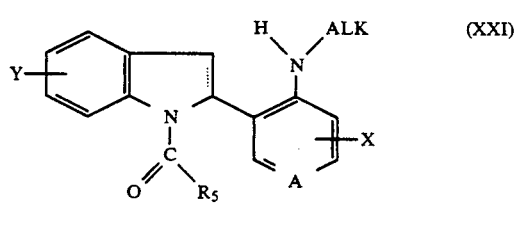 (XXI)

or

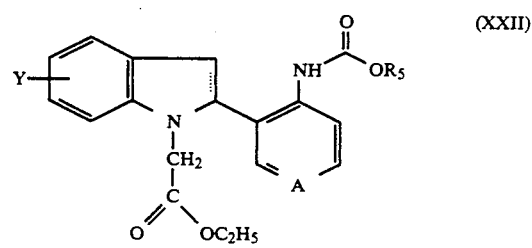 (XXII)

Compounds of Formula I according to this invention are useful as topical agents for the treatment of skin disorders. The dermatological activities of the compounds of this invention were ascertained with reference to the following methods.

DERMATOLOGICAL TEST METHODS

Phospholipase $A_2$-indouced Paw Edema (PIPE)

The ability of compounds to prevent naja naja (snake venom) phospholipase $A_2$-induced paw edema in male Wistar rats (100–125 g) was measured. $PLA_2$ (3 units/paw) alone or with 0.1M of the test compound was injected in the subplantar region of the rat left hindpaw. Immediately subsequent to the injection and at two hours post administration the paw was immersed in a mercury bath, and paw displacement was measured on a recorder via a transducer. (Standard: hydrocortisone $ED_{50}=0.46M$). See Giessler, A.J. et al., *Agents and Actions*, Vol. 10, Trends in Inflammation Research (1981), p. 195.

Arachidonic Acid-Induced Ear Edema (AAEE)

The purpose of this assay was to determine the ability of a topically-applied compound to prevent mouse ear edema induced by topical application of arachidonic acid. Female Swiss Webster mice topically received vehicle or test compound (1.0 mg/ear) on both ears (10 µl on outer and inner ears). After 30 minutes, the right ear of all groups received arachidonic acid (4 mg/ear) and the left ear received vehicle alone. After an additional 1 hour, the mice were sacrificed and an ear punch (4 mm) was taken from each ear. The difference in right and left ear punch weights for each animal was determined to assess activity. (Standard: indomethacin $ED_{50} = 1.5$ mg/ear). See Young, J.M. et al., *Invest. Dermatol.*, 80, (1983), pp 48–52.

TPA-Induced Ear Edema (TPAEE)

The purpose of this assay was to determine the ability of a topically-applied compound to prevent ear edema induced by topical application of TPA (phorbol 12-myristate acetate). Female Swiss Webster mice topically received TPA (10 µg/ear) on the right ear and vehicle on the left ear. The test compound (10 µg/ear) was applied to both ears. After five hours, the animals were sacrificed and an ear punch (4 mm) was taken from each ear. The difference in right and left ear punch weights for each animal was determined to assess activity. (Standard: hydrocortisone $ED_{50} = 47$ µg/ear). See Young, J.M. et al., *J. Invest. Dermatol.*, 80 (1983), pp. 48–52.

Dermatological activities for some of the compounds of this invention are presented in Table 1.

TABLE 1

| Compound | PIPE* @ 0.1 M | TPAEE* @ 10 µg | AAEE* @ 1 mg |
| --- | --- | --- | --- |
| 2-(2-amino-5-chlorophenyl)-2,3-dihydro-1H-indole | −55% | | −36% |
| 2-(2-amino-5-methoxyphenyl)-1H-indole | | −60% | |
| 2,2-dimethyl-N-[2-(1H-indol-2-yl)phenyl]propanamide | −43% | | |
| 2,2-dimethyl-N-[2,3-dihydro-1H-indol-2-yl)phenyl]propanamide | −51% | | |
| 2-(2-aminophenyl)-5-methoxy-2,3-dihydro-1H-indole | −48% | | |
| 1-(1,1-dimethylethoxycarbonyl)-2-(2-aminophenyl)-2,3-dihydro-1H-indole | −46% | −49% | |
| 2-[2-(octyloxycarbonylamino)-phenyl]-2,3-dihydro-1H-indole | | | −43% |

*difference in edema vs. control

Examples of the compound of this invention include:
2-(4-amino-3-pyridinyl)-1H-indole;
2-(2-aminophenyl)-5-methoxy-1H-indole;
2-(2-amino-5-methoxyphenyl)-1H-indole;
2-(2-amino-4-trifluoromethylphenyl)-1H-indole;
N-[2-(1H-indol-2-yl)-4-chlorophenyl]formamide;
2-(2-methylamino-5-chlorophenyl)-1H-indole;
2,2-dimethyl-N-[2-(1H-indol-2-yl)phenyl]propanamide;
2-[4-(octyloxycarbonyl)amino-3-pyridinyl]-1H-indole;
2-(2-aminophenyl)-2,3-dihydro-1H-indole;
2-(2-amino-5-chlorophenyl)-2,3-dihydro-1H-indole;
2-(2-aminophenyl)-5-methoxy-2,3-dihydro-1H-indole;
2-(2-amino-5-methoxyphenyl)-2,3-dihydro-1H-indole;
2,3-dihydro-2-(2-methylamino-5-chlorophenyl)-1H-indole;
2,3-dihydro-2-(2-amino-4-trifluoromethylphenyl)-1H-indole;
2-(2-aminophenyl)-5-hydroxy-2,3-dihydro-1H-indole;
2,2-dimethyl-N-[2-(2,3-dihydro-1H-indol-2-yl)phenyl]propanamide;
2,2-dimethyl-N-[2-(5-methoxy-2,3-dihydro-1H-indol-2-yl)phenyl]propanamide;
2,2-dimethyl-N-[2-(2,3-dihydro-1H-indol-2-yl)-4-chlorophenyl]propanamide;
2,2-dimethyl-N-[2-(5-bromo-2,3-dihydro-1H-indol-2-yl)phenyl]propanamide;
2-[2-(methoxycarbonylamino)phenyl]-2,3-dihydro-1H-indole
2-[2-(octyloxycarbonylamino)phenyl]-2,3-dihydro-1H-indole;
2,2-dimethyl-N-[2-(2,3-dihydro-1-methyl-1H-indol-2-yl)phenyl]propanamide;
1-(1,1-dimethylethoxycarbonyl)-2-(2-aminophenyl)-2,3-dihydro-1H-indole;
2,2-dimethyl-N-[2-(1-acetyl-2,3-dihydro-1H-indol-2-yl)phenyl]propanamide;
2,2-dimethyl-N-[2-(1-acetyl-2,3-dihydro-1H-indol-2-yl)-4-chlorophenyl]propanamide;
2,2-dimethyl-N-[2-[2,3-dihydro-1-(ethoxycarbonyl)methyl-1H-indol-2-yl]phenyl]propanamide;
2,2-dimethyl-N-[4-chloro-2-[2,3-dihydro-1-(ethoxycarbonyl)methyl-1H-indol-2-yl]phenyl]propanamide;
1-methoxycarbonyl-2-[2-(methoxycarbonyl)aminophenyl]-2,3-dihydro-1H-indole;
1-(2,2-dimethylethoxycarbonyl)-2-[2-(1,1-dimethylethoxycarbonyl)aminophenyl]-2,3-dihydro-1H-indole;
2-(2-amino-3-pyridinyl)-2,3-dihydro-1H-indole;
2-(2-amino-5-hydroxyphenyl)-2,3-dihydro-1H-indole;
2-(2-amino-5-bromophenyl)-2,3-dihydro-1H-indole;
2-(2-amino-4-fluorophenyl)-2,3-dihydro-1H-indole;
2-(2-amino-3-methylphenyl)-2,3-dihydro-1H-indole;
2-(2-aminophenyl)-2,3-dihydro-5-nitro-1H-indole;
2-(2-aminophenyl)-5-amino-2,3-dihydro-1H-indole;
2-(2-aminophenyl)-4-chloro-2,3-dihydro-1H-indole;
2-(2-amino-5-bromphenyl)-4-chloro-2,3-dihydro-1H-indole;
2-(2-aminophenyl)-6-chloro-2,3-dihydro-1H-indole;
2-[2-phenoxycarbonyl)amino-4-(trifluoromethyl)phenyl]-2,3-dihydro-1H-indole;
2-[2-(1,1-dimethylethoxycarbonyl)amino-5-chlorophenyl]-2,3-dihydro-1H-indole; and
2-(2-amino-5-chlorophenyl)-2,3-dihydro-5-methoxy-1H-indole;

The following examples are presented in order to illustrate this invention:

EXAMPLE 1

1-(4-Amino-3-pyridinyl)ethanone

To a solution of 17.72 g (4-amino-3-pyridyl)carbonitrile in 400 ml THF (tetrahydrofuran) at 0° C. was added dropwise 200 ml 3.0M methylmagnesium chloride in THF. After the addition was complete, the reaction mixture was allowed to come to room temperature and stirred twenty-four hours. The reaction was quenched with water. Saturated oxalic acid solution (350 ml) was added, and the mixture was then refluxed for one and a half hours. This mixture was made basic with dilute NaOH solution, and extracted with EtOAc. The extracts were washed with saturated NaCl solution, dried (MgSO$_4$), and concentrated to yield 16.14 g solid. Purification of 1.5 g by flash chromatography and recrystallization from toluene yielded 0.71 g solid, m.p. 161°–163° C.

| ANALYSIS: | | | |
|---|---|---|---|
| Calculated for C$_7$H$_8$N$_2$O: | 61.75% C | 5.92% H | 20.57% N |
| Found: | 62.09% C | 5.83% H | 20.34% N |

EXAMPLE 2

1-(4-Amino-3-pyridinyl)ethanone phenylhydrazone

Phenylhydrazine (4.0 ml) was added to 5.00 g 1-(4-amino-3-pyridinyl)ethanone, and the mixture was stirred at 100° C. for seventeen hours. A similar procedure was followed using 4.0 g 1-(4-amino-3-pyridinyl)ethanone and 3.20 ml phenylhydrazine. The products of the two reactions were combined and purified by flash chromatography to yield 9.74 g solid. Recrystallization of 1.24 g from CH$_3$OH/water yielded 0.28 g solid, m.p. 168°–170° C.

| ANALYSIS: | | | |
|---|---|---|---|
| Calculated for C$_{13}$H$_{14}$N$_4$: | 69.00% C | 6.24% H | 24.76% N |
| Found: | 68.78% C | 6.27% H | 24.53% N |

EXAMPLE 3

2-Aminoacetophenone 3-chlorophenylhydrazone

A mixture of 3.12 g 2-aminoacetophenone and 3.29 g 3-chlorophenylhydrazine in 4 ml HOAc and 20 ml EtOH was refluxed for one hour. The cooled reaction mixture was diluted with water and the precipitate was collected, washed with water, and dried to give 5.16 g solid. Recrystallization from methanol gave 2.12 g solid, m.p. 131°–134° C.

| ANALYSIS: | | | |
|---|---|---|---|
| Calculated for C$_{14}$H$_{14}$ClN$_3$: | 64.74% C | 5.43% H | 16.18% N |
| Found: | 64.41% C | 5.38% H | 16.00% N |

EXAMPLE 4

2-Aminoacetophenone 4-chlorophenylhydrazone

A mixture of 10.43 g 2-aminoacetophenone and 11.0 g 4-chlorophenylhydrazine in 30 ml EtOH and 10 ml HOAc was refluxed for one hour. The cooled reaction mixture was diluted with water and the precipitate was collected, washed with water, and dried to give 16.83 g solid. Recrystallization from methanol gave 3.48 g solid, m.p. 109°–112° C.

| ANALYSIS: | | | |
|---|---|---|---|
| Calculated for C$_{14}$H$_{14}$ClN$_3$: | 64.74% C | 5.43% H | 16.18% N |
| Found: | 64.92% C | 5.40% H | 16.17% N |

EXAMPLE 5

2-Amino-5-bromoacetophenone 3-chlorophenylhydrazone

A mixture of 3.77 g 2-amino-5-bromoacetophenone and 2.59 g 3-chlorophenylhydrazine in 20 ml EtOH and 4 ml HOAc was refluxed for forty-five minutes. The cooled reaction mixture was diluted with 120 ml of water, and the precipitate was collected, washed with water, and dried to give 5.40 g solid. Recrystallization from methanol gave 1.42 g solid, m.p. 115°–117° C.

| ANALYSIS: | | | |
|---|---|---|---|
| Calculated for C$_{14}$H$_{13}$BrClN$_3$: | 49.66% C | 3.81% H | 12.41% N |
| Found: | 49.61% C | 4.07% H | 12.21% N |

EXAMPLE 6

2-Amino-5-bromoacetophenone-4-chlorophenylhydrazone

A mixture of 2.00 g 2-amino-5-bromoacetophenone and 1.34 g 4-chlorophenylhydrazine in 6 ml HOAc and 15 ml EtOH was refluxed for forty-five minutes. The cooled reaction mixture was diluted with water and the precipitate was collected, washed with water, and dried to give 2.83 g. Recrystallization from methanol gave 1.42 g solid, m.p. 191°–193° C.

| ANALYSIS: | | | |
|---|---|---|---|
| Calcualted for C$_{14}$H$_{13}$BrClN$_3$: | 49.66% C | 3.87% H | 12.41% N |
| Found: | 49.39% C | 3.85% H | 12.19% N |

EXAMPLE 7

2-Aminoacetophenone-4-methoxyphenylhydrazone p-Methoxyphenylhydrazine was produced in situ by titration of 10 g p-methoxyphenylhydrazine.HCl in 65 ml EtOH with a 21 weight % solution of sodium ethoxide in EtOH using phenolphthalein indicator. Acetic acid (12 ml) and 7.04 g 2-aminoacetophenone were added and the resultant mixture was then refluxed for one hour. The cooled reaction mixture was diluted with water, and the precipitate was collected, washed with water and hexane, and dried to give 10.01 g solid, m.p. 99°–103° C. (dec).

| ANALYSIS: | | | |
|---|---|---|---|
| Calcualted for C$_{15}$H$_{17}$N$_3$O: | 70.56% C | 6.71% H | 16.46% N |
| Found: | 70.29% C | 6.63% H | 16.02% N |

EXAMPLE 8

2-Amino-5-chloroacetophenone 4-methoxyphenylhydrazone p-Methoxyphenylhydrazine was produced in situ by addition of 30 ml of a 21 weight % solution of sodium ethoxide in EtOH to 11.32 g p-methoxyphenylhydrazine.HCl in 80 ml EtOH using phenolphthalein as an indicator.

To the above mixture were added 38 ml HOAc and 10 g 2-amino-5-chloroacetophenone, and this was then refluxed for one and a half hours. The cooled reaction mixture was diluted with water, and the resulting precipitate was collected, washed with water and hexane, and dried to give 14.05 g solid. Recrystallization from MeOH/water yielded 7.60 g solid, m.p. 124°–128° C. (dec).

ANALYSIS:

| | | | |
|---|---|---|---|
| Calculated for $C_{15}H_{16}ClN_3O$: | 62.18% C | 5.57% H | 14.50% N |
| Found: | 62.16% C | 5.45% H | 14.15% N |

EXAMPLE 9

2-Amino-5-methoxyacetophenone phenylhydrazone

A mixture of 8.3 g 2-amino-5-methoxyacetophenone, 5.2 ml phenylhydrazine, 3 ml HOAc and 25 ml EtOH was refluxed for one hour. On cooling a precipitate formed. This was collected, washed with EtOH and hexane, and dried to give 8.9 of solid, m.p. 118°–120° C.

ANALYSIS:

| | | | |
|---|---|---|---|
| Calculated for $C_{15}H_{17}N_3O$: | 70.56% C | 6.71% H | 16.46% N |
| Found: | 70.29% C | 6.74% H | 16.45% N |

EXAMPLE 10

2-Amino-4-trifluoromethylacetophenone phenylhydrazone

To a solution of 4.50 g 2-amino-4-trifluoromethylacetophenone and 10 ml acetic acid in 70 ml EtOH was added 2.4 ml phenylhydrazine. The resulting solution was refluxed two and a half hours. Upon dilution with ice, the cooled reaction mixture precipitated a solid which was washed with water and hexane. Recrystallization from MeOH/water yielded 2.58 g solid, m.p. 129°–132° C.

ANALYSIS:

| | | | |
|---|---|---|---|
| Calculated for $C_{15}H_{14}F_3N_3$: | 61.43% C | 4.81% H | 14.33% N |
| Found: | 61.29% C | 4.90% H | 14.38% N |

EXAMPLE 11

2-Acetamido-5-chloroacetophenone 4-methoxyphenylhydrazone p-Methoxyphenylhydrazine was produced in situ by addition of 25 ml of a 21 weight % solution of sodium ethoxide in EtOH to 9.07 g p-methoxyphenylhydrazine.HCl in 100 ml EtOH using phenolphthalein as an indicator.

To the above mixture were added 28 ml HOAc and then 10.00 g 2-acetamido-5-chloroacetophenone. The mixture was refluxed two hours, and the cooled reaction mixture was diluted with water to precipitate a solid. This was then collected, washed with water and hexane, and recrystallized from MeOH to yield 3.16 g solid, m.p. 190°–195° C. dec.

ANALYSIS:

| | | | |
|---|---|---|---|
| Calculated for $C_{17}H_{18}ClN_3O_2$: | 61.54% C | 5.47% H | 12.66% N |
| Found: | 61.38% C | 5.54% H | 12.56% N |

EXAMPLE 12

2-(4-Amino-3-pyridinyl)-1H-indole 1-(4-Amino-3-pyridinyl)ethanone phenylhydrazone (4.5 g) was added portionwise to 90 g polyphosphoric acid at 100° C. under nitrogen. After the addition was complete, the temperature was adjusted to 125° C., and the mixture stirred an additional one and a half hours. The mixture was added to water, made basic with 38% NH4OH, and extracted with ethyl acetate. The extracts were combined, washed with saturated NaCl solution, and concentrated to give 4.13 g solid. Purification of 2.23 g by flash chromatography using 10% methanol/dichloromethane yielded 1.37 g solid. This was combined with 0.85 g, which had been prepared by a similar procedure, dissolved in ethanol, and concentrated to yield 1.82 g solid, m.p. 230°–233° C.

ANALYSIS:

| | | | |
|---|---|---|---|
| Calculated for $C_{13}H_{11}N_3$: | 74.62% C | 5.30% H | 20.08% N |
| Found: | 74.05% C | 5.42% H | 19.68% N |

EXAMPLE 13

2-(2-Aminophenyl)-5-methoxy-1H-indole

A solution of 22.41 g 2-aminoacetophenone 4-methoxyphenylhydrazone in 475 ml ethylene glycol was refluxed for one day. The cooled solution was diluted with water, and the precipitate was collected and washed with water and hexane to yield 34.75 g solid. Trituration of 10 g with warm ethanol yielded 2.55 g solid, shrinking 186° C., m.p. 198°–200° C.

ANALYSIS:

| | | | |
|---|---|---|---|
| Calculated for $C_{15}H_{14}N_2O$: | 75.61% C | 5.92% H | 11.76% N |
| Found: | 75.54% C | 6.00% H | 11.63% N |

EXAMPLE 14

2-(2-Amino-5-methoxyphenyl)-1H-indole

To polyphosphoric acid (30 ml) preheated to 110° C. was added 1.95 g 1-(2-amino-5-methoxyphenyl)ethanone phenylhydrazone in small portions under N2. The reaction was maintained at 110°–120° C. for forty-five minutes. This mixture was poured directly into excess water and made basic with concentrated NH4OH. Extraction with dichloromethane, drying (MgSO4) and concentration yielded 1.5 g 2-(2-amino-5-methoxyphenyl)-1H-indole as a solid, m.p. 97°–99° C.

To a solution of 1.8 g 2-(2-amino-5-methoxyphenyl)-1H-indole in 60 ml acetic acid at 15° was added 1.8 g NaCNBH3 and this mixture was stirred at room temperature overnight. After pouring into excess 50% NaOH in ice, extraction with CH2Cl2, drying (MgSO4), concentration and flash chromatography using CH2Cl2 as an eluent gave 0.6 g solid, m.p. 99°–101°.

ANALYSIS:

| | | | |
|---|---|---|---|
| Calculated for $C_{15}H_{14}N_2O$: | 75.61% C | 5.92% H | 11.76% N |
| Found: | 75.57% C | 6.00% H | 11.58% N |

EXAMPLE 15

2-(2-Amino-4-trifluoromethylphenyl)-1H-indole

2-Amino-4-trifluoromethylacetophenone phenylhydrazone (10 g) was added portionwise to 200 ml polyphosphoric acid at 120° C. under N2. The temperature was kept between 120° C. and 140° C. After the addition was complete, the mixture was stirred thirty additional minutes at the above temperature and then added directly to excess water with stirring. The precipitated solid was collected and triturated with a 1:1 NH₄OH/water solution. The resulting solid was collected, washed with water and hexane, and dried. Purification by flash chromatography yielded a solid, which was recrystallized from EtOH/water to give 2.66 g solid, m.p. 164°–166° C.

| ANALYSIS: | | | |
|---|---|---|---|
| Calculated for $C_{15}H_{11}F_3N_2$: | 65.22% C | 4.01% H | 10.14% N |
| Found: | 65.10% C | 3.94% H | 10.09% N |

EXAMPLE 16

N-[2-(1H-Indol-2-yl)-4-chlorophenyl]formamide

To a solution of 10.0 g 2-(2-amino-4-chlorophenyl)indole in 230 ml THF, were added 5.4 ml formic acid and 11.1 g 1,3-dicyclohexylcarbodiimide. The resulting mixture was stirred one day at room temperature. It was then filtered, washed with 7.5% NaHCO₃, water and saturated NaCl solution, dried (MgSO₄), and concentrated to give a gum. Purification by flash chromatography yielded 4.84 g solid. Recrystallization from ethanol/water yielded 2.72 g solid, m.p. 129°–131° C.

| ANALYSIS: | | | |
|---|---|---|---|
| Calculated for $C_{15}H_{11}ClN_2O$: | 66.55% C | 4.10% H | 10.35% N |
| Found: | 66.12% C | 4.10% H | 10.34% N |

EXAMPLE 17

2-(2-Methylamino-5-chlorophenyl)-1H-indole

A total of 123 ml 1M LiAlH₄ in THF was added portionwise to a solution of 15.37 g N-[2-(1H-indol-2-yl)-4-chlorophenyl]formamide in 230 ml THF, during which the temperature was maintained below 20° C. The resulting mixture was stirred three hours at room temperature and then quenched with a saturated NH₄Cl solution (140 ml). This was then filtered through celite, dried (MgSO₄), and concentrated to yield a solid. Purification by HPLC using CH₂Cl₂/hexane (2:3) as eluent yielded 7.43 g solid, m.p. 123°–126°.

| ANALYSIS: | | | |
|---|---|---|---|
| Calculated for $C_{15}H_{13}ClN_2$: | 70.18% C | 5.10% H | 10.91% N |
| Found: | 70.17% C | 5.07% H | 10.92% N |

EXAMPLE 18

2,2-Dimethyl-N-[2-(1H-indol-2-yl)phenyl]propanamide

To a mixture of 5.00 g 2-(2-aminophenyl)-1H-indole, 13.08 g NaOAc.3H₂O, 35 ml water and 200 ml HOAc was added dropwise 3.27 ml trimethylacetyl chloride at 15° C. After the addition was complete, the reaction mixture was stirred for one hour at room temperature. Upon addition of water, a brown gum precipitated, which was extracted into CH₂Cl₂. The organic phase was washed with H₂O, 7.5% NaHCO₃, and saturated NaCl, dried (MgSO₄), and concentrated to yield 5.87 g gum. Flash chromatography using CH₂Cl₂ yielded 3.12 g solid, m.p. 132°–136° C.

| ANALYSIS: | | | |
|---|---|---|---|
| Calculated for $C_{19}H_{20}N_2O$: | 78.05% C | 6.89% H | 9.58% N |
| Found: | 77.71% C | 6.90% H | 9.53% N |

EXAMPLE 19

2-[4-(Octyloxycarbonyl)amino-3-pyridinyl]-1H-indole

To a solution of 1.00 g 2-(4-amino-3-pyridinyl)-1H-indole and 1.30 ml triethylamine in 30 ml THF at 0° C. was added dropwise 0.95 g octyl chloroformate. The solution was stirred for six hours at room temperature and then quenched with water. The solution was extracted with ethyl acetate, and the extracts were combined, washed with saturated NaCl solution, dried (MgSO₄) and concentrated to yield 1.76 g solid. A similar procedure using 0.20 g 2-(4-amino-3-pyridinyl)-1H-indole yielded 0.33 g solid. The products from the two reactions were combined and recrystallized from MeOH to yield 1.26 g solid, m.p. 157°–159° C.

| ANALYSIS: | | | |
|---|---|---|---|
| Calculated for $C_{22}H_{27}N_3O_2$: | 72.30% C | 7.45% H | 11.50% N |
| Found: | 72.39% C | 7.48% H | 11.50% N |

EXAMPLE 20

2-(2-Aminophenyl)-2,3-dihydro-1H-indole

Sodium cyanoborohydride (6.4 g) was added in several portions to a solution of 6.0 g 2-(2-aminophenyl)-1H-indole in 200 ml HOAc at 5° C. The resulting solution was stirred at room temperature overnight. Water was added and the reaction mixture was concentrated. The residue was diluted with ice water and made basic with 50% NaOH. This mixture was extracted with Et₂O and the extracts were washed with water and saturated NaCl solution, and dried (MgSO₄). Concentration gave 6.1 g crude product which was chromatographed by HPLC to give 3.05 g solid, m.p. 115°–117° C.

| ANALYSIS: | | | |
|---|---|---|---|
| Calculated for $C_{14}H_{14}N_2$: | 79.96% C | 6.71% H | 13.33% N |
| Found: | 79.88% C | 6.77% H | 13.12% N |

EXAMPLE 21

2-(2-Amino-5-chlorophenyl)-2,3-dihydro-1H-indole

Sodium cyanoborohydride (6.37 g) was added portionwise to a solution of 7.00 g 2-(2-amino-5-chlorophenyl)-1H-indole in 245 ml HOAc at 15° C. The resulting solution was stirred at room temperature for one day. The reaction mixture was diluted and made basic by addition of 50% NaOH in ice. The mixture was extracted with Et₂O, and the extracts were washed with water and saturated NaCl solution, and dried (MgSO₄). Concentration gave 6.48 g gum which was chromatographed by HPLC using CH₂Cl₂/hexane (7:3) as eluent to give 2.56 g solid, m.p. 107°–109° C.

| ANALYSIS: | | | |
|---|---|---|---|
| Calculated for $C_{14}H_{13}ClN_2$: | 68.71% C | 5.35% H | 11.45% N |

| ANALYSIS: | | | |
|---|---|---|---|
| Found: | 68.52% C | 5.34% H | 11.30% N |

EXAMPLE 22

2-(2-Aminophenyl)-5-methoxy-2,3-dihydro-1H-indole

Sodium cyanoborohydride (19.30 g) was added portionwise to a solution of 20.50 g 2-(2-aminophenyl)-5-methoxy-1H-indole in 1500 ml acetic acid at 15° C. The resulting solution was stirred at room temperature for one day. The reaction mixture was diluted and made basic by addition of 50% NaOH in ice. The mixture was extracted with ethyl acetate, and the extracts were washed with saturated NaCl solution and dried (MgSO$_4$). Concentration yielded 20.56 g solid. Purification of a 10 g portion by HPLC yielded 2.33 g solid, m.p. 94°-98° C. (dec.).

| ANALYSIS: | | | |
|---|---|---|---|
| Calculated for C$_{15}$H$_{16}$N$_2$O: | 74.97% C | 6.71% H | 11.66% N |
| Found: | 74.94% C | 6.86% H | 11.49% N |

EXAMPLE 23

2-(2-Amino-5-methoxyphenyl)-2,3-dihydro-1H-indole

To polyphosphoric acid (30 ml) preheated to 110° C. was added 1.95 g 1-(2-amino-5-methoxyphenyl)ethanone phenylhydrazone in small portions under nitrogen. The reaction was maintained at 110°-120° C. for forty-five minutes. This mixture was poured directly into excess water and made basic with concentrated NH$_4$OH. Extraction with CH$_2$Cl$_2$, drying (MgSO$_4$) and concentration yielded 1.5 g 2-(2-amino-5-methoxyphenyl)-1H-indole as a solid, m.p. 97°-99° C.

To a solution of 1.8 g 2-(2-amino-5-methoxyphenyl)-1H-indole in 60 ml acetic acid at 15° was added 1.8 g NaCNBH$_3$ and this mixture was stirred at room temperature overnight and thereafter poured into excess 50% NaOH in ice. Extraction with CH$_2$Cl$_2$, drying (MgSO$_4$), concentration and flash chromatography using 1% EtOAc/CH$_2$Cl$_2$ as an eluent gave 0.23 g solid, m.p. 120°-123° C.

| ANALYSIS: | | | |
|---|---|---|---|
| Calculated for C$_{15}$H$_{16}$N$_2$O: | 74.97% C | 6.71% H | 11.66% N |
| Found: | 74.48% C | 6.63% H | 11.32% N |

EXAMPLE 24

2,3-Dihydro-2-(2-methylamino-5-chlorophenyl)-1H-indole

Sodium cyanoborohydride (4.72 g) was added portionwise to a solution of 5.36 g 2-(2-methylamino-5-chlorophenyl)-1H-indole in 160 ml HOAc at 10° C. The mixture was stirred twenty hours at room temperature. It was then diluted and added to excess 50% NaOH in ice. The mixture was extracted with CH$_2$Cl$_2$, and the extracts were washed with saturated NaCl solution and dried (MgSO$_4$). Concentration yielded 5.31 g solid. Purification by HPLC using CH$_2$Cl$_2$/hexane (1:1) as eluent yielded 2.65 g solid, m.p. 106°-108° C.

| ANALYSIS: | | | |
|---|---|---|---|
| Calculated for C$_{15}$H$_{15}$ClN$_2$: | 69.63% C | 5.84% H | 10.83% N |
| Found: | 69.75% C | 5.87% H | 10.61% N |

EXAMPLE 25

2,3-Dihydro-2-(2-amino-4-trifluoromethylphenyl)-1H-indole

Borane-tetrahydrofuran complex (1.0M, 130 ml) was added dropwise to a solution of 90 ml THF and 90 ml TFA (trifluoroacetic acid) at −5° C., and then 17.93 g 2-(2-amino-4-trifluoromethylphenyl)-1H-indole was added. The resulting solution was stirred at room temperature overnight. The reaction mixture was quenched with water and basified with 50% NaOH. The solution was extracted with Et$_2$O. This organic layer was washed with water and saturated NaCl solution, dried (MgSO$_4$), and concentrated to yield 3.65 g solid. Purification by HPLC and recrystallization from MeOH/water yielded 1.93 g solid, m.p. 152°-154° C.

| ANALYSIS: | | | |
|---|---|---|---|
| Calculated for C$_{15}$H$_{13}$F$_3$N: | 64.74% C | 4.71% H | 10.07% N |
| Found: | 64.67% C | 4.63% H | 9.95% N |

EXAMPLE 26

2-(2-Aminophenyl)-5-hydroxy-2,3-dihydro-1H-indole

A solution of 5.25 g 2-(2-aminophenyl)-5-methoxy-2,3-dihydro-1H-indole in 115 ml CH$_2$Cl$_2$ was added dropwise to 90.4 ml 1.0M BBr$_3$ in CH$_2$Cl$_2$ at 0° C. The solution was stirred at 0°-5° C. for one hour, and then quenched by dropwise addition of 135 ml water. A total of 400 ml 7.5% NaHCO$_3$ was added dropwise, and the resulting solution was stirred 30 minutes. It was then basified to a pH of ~9 with K$_2$CO$_3$ and extracted with EtOAc. The extracts were washed with saturated NaCl solution, dried (MgSO$_4$), and concentrated to yield 5.10 g solid. Trituration with 5% EtOAc/CH$_2$Cl$_2$ and recrystallization from MeOH/water yielded 1.00 g solid, m.p. 169°-171° C.

| ANALYSIS: | | | |
|---|---|---|---|
| Calculated for C$_{14}$H$_{14}$N$_2$O: | 74.31% C | 6.24% H | 12.38% N |
| Found: | 74.21% C | 6.25% H | 12.39% N |

EXAMPLE 27

2,2-Dimethyl-N-[2-(2,3-dihydro-1H-indol-2-yl)phenyl]-propanamide

Trimethylacetyl chloride (3.6 ml) was added dropwise to a solution of 5.8 g 2-(2-aminophenyl)-2,3-dihydro-1H-indole and 4.3 ml Et$_3$N in 75 ml CH$_2$Cl$_2$ with ice bath cooling. The resulting mixture was stirred at room temperature for thirty minutes and then quenched with water. The organic extract was washed with water, saturated NaHCO$_3$ solution and saturated NaCl solution and dried (MgSO$_4$). Concentration gave 7.7 g crude product which was flash chromatographed using CH$_2$Cl$_2$ as eluent to give 4.9 g solid, m.p. 175°-178° C.

| ANALYSIS: | | | |
|---|---|---|---|
| Calculated for $C_{19}H_{22}N_2O$: | 77.51% C | 7.53% H | 9.52% N |
| Found: | 77.67% C | 7.52% H | 9.65% N |

EXAMPLE 28

2,2-Dimethyl-N-[2-(5-methoxy-2,3-dihydro-1H-indol-2-yl)phenyl]propanamide

Trimethylacetyl chloride (2.40 ml) was added dropwise to a solution of 4.68 g 2-(2-aminophenyl)-5-methoxy-2,3-dihydro-1H-indole and 3.00 ml $Et_3N$ in 150 ml $CH_2Cl_2$ at 0° C. The resulting mixture was stirred at room temperature for two hours and then quenched with water. The organic extract was washed with 7.5% $NaHCO_3$ and sat. NaCl solution, dried ($MgSO_4$), and concentrated to yield 5.59 g crystalline solid. Recrystallization from MeOH/water yielded 2.38 g solid, m.p. 117°–119° C.

| ANALYSIS: | | | |
|---|---|---|---|
| Calculated for $C_{20}H_{24}N_2O_2$: | 74.05% C | 7.46% H | 8.63% N |
| Found: | 74.15% C | 7.48% H | 8.65% N |

EXAMPLE 29

2,2-Dimethyl-N-[2-(2,3-dihydro-1H-indol-2-yl)4-chlorophenyl]propanamide

To a solution of 5.00 g 2-(2-amino-5-chlorophenyl)-2,3-dihydro-1H-indole in 70 ml $CH_2Cl_2$ at 10° C. were added 3.14 ml triethylamine and then dropwise 2.52 ml trimethylacetylchloride. The resulting solution was stirred for one hour at 10° C. and then quenched with water. The organic phase was separated, washed with 7.5% $NaHCO_3$ and saturated NaCl, dried ($MgSO_4$), and concentrated to yield 5.67 g solid. Recrystallization from cyclohexane yielded 3.09 g solid, m.p. 195°–198° C.

| ANALYSIS: | | | |
|---|---|---|---|
| Calculated for $C_{19}H_{21}ClN_2O$: | 69.39% C | 6.44% H | 8.52% N |
| Found: | 69.37% C | 6.44% H | 8.35% N |

EXAMPLE 30

2,2-Dimethyl-N-[2-(5-bromo-2,3-dihydro-1H-indol-2-yl)phenyl]propanamide

A solution of 4.0 g N-bromosuccinimide in 40 ml anhydrous DMF (dimethylformamide) was added dropwise at 5° C. (ice bath) over 20 minutes to a solution of 6.0 g 2,2-dimethyl-N-[2-(2,3-dihydro-1H-indol-2-yl)phenyl]propanamide in 60 ml DMF. After stirring for one hour additionally, the resulting solution was poured into excess water and the precipitated solid was collected, washed, and taken up in $Et_2O$. The extract was washed with water and brine, dried ($MgSO_4$) and concentrated to give 7.2 g solid. Recrystallization from cyclohexane gave 2.2 g needles, m.p. 173°–175° C.

| ANALYSIS: | | | |
|---|---|---|---|
| Calculated for $C_{19}H_{21}BrN_2O$: | 61.13% C | 5.67% H | 7.51% N |

| -continued | | | |
|---|---|---|---|
| ANALYSIS: | | | |
| Found: | 60.97% C | 5.71% H | 7.41% N |

EXAMPLE 31

2-[2-(Methoxycarbonylamino)phenyl]-2,3-dihydro-1H-indole

Methyl chloroformate (3.80 ml) was added dropwise to a solution of 10.34 g 2-(2-aminophenyl)-2,3-dihydro-1H-indole and 8.40 ml pyridine in 190 ml $CH_2Cl_2$ at 0° C. The solution was stirred five and a half hours at 0° C., and then quenched with water. The organic layer was separated, washed with 5% HCl and saturated NaCl solution, dried ($MgSO_4$), and concentrated to yield 7.92 g solid. A similar procedure using 3.00 g 2-(2-aminophenyl)-2,3-dihydro-1H-indole yielded 1.67 g solid. The solids from the two reactions were combined and purified by HPLC. Recrystallization from MeOH/water yielded 2.20 g solid, m.p. 125°–128° C.

| ANALYSIS: | | | |
|---|---|---|---|
| Calculated for $C_{16}H_{16}N_2O_2$: | 71.62% C | 6.01% H | 10.44% N |
| Found: | 71.79% C | 6.05% H | 10.43% N |

EXAMPLE 32

2-[2-(Octyloxycarbonylamino)phenyl]-2,3-dihydro-1H-indole

Octyl chloroformate (2.00 ml) was added dropwise to a solution of 2.15 g 2-(2-aminophenyl)-2,3-dihydro-1H-indole and 2.00 ml pyridine in 35 ml $CH_2Cl_2$ at 0° C. The solution was stirred five hours at 0° C. and then quenched with water. The organic layer was separated, washed with 5% HCl and saturated NaCl solution, dried ($MgSO_4$), and concentrated to yield a solid. Purification by flash chromatography using $CH_2Cl_2$/hexane (1:2) as eluent gave 1.74 g solid, m.p. 99°–102° C.

| ANALYSIS: | | | |
|---|---|---|---|
| Calculated for $C_{23}H_{30}N_2O_2$: | 75.38% C | 8.25% H | 7.64% N |
| Found: | 75.31% C | 8.29% H | 7.30% N |

EXAMPLE 33

2,2-Dimethyl-N-[2-(2,3-dihydro-1-methyl-1H-indol-2-yl)phenyl]propanamide

To a mixture of 9.40 g $K_2CO_3$ and 10.05 g 2,2-dimethyl-N-[2-(2,3-dihydro-1H-indol-2yl)phenyl]propanamide in 125 ml DMF at 0° C., was added 3.64 ml iodomethane. The resulting mixture was stirred twenty-eight hours at room temperature. Upon dilution with water, a solid precipitated, which was collected and washed with water. Recrystallization from EtOH/water yielded 4.86 g solid, m.p. 133°–135° C.

| ANALYSIS: | | | |
|---|---|---|---|
| Calculated for $C_{20}H_{24}N_2O$: | 77.89% C | 7.84% H | 9.08% N |
| Found: | 77.92% C | 7.95% H | 9.08% N |

EXAMPLE 34

1-(1,1-Dimethylethoxycarbonyl)-2-(2-aminophenyl)-2,3-dihydro-1H-indole

A solution of 5.20 g di-tert-butyl dicarbonate in 25 ml $CH_2Cl_2$ was added dropwise to a solution of 5.00 g 2-(2-aminophenyl)-2,3-dihydro-1H-indole in $CH_2Cl_2$ at 10° C. The resulting solution was stirred for two and a half hours at room temperature. It was then washed with 5% NaOH and sat. NaCl solution, dried ($MgSO_4$), and concentrated to yield a solid. Purification by HPLC using $CH_2Cl_2$ yielded 3.71 g solid, m.p. 114°–117° C.

| ANALYSIS: | | | |
|---|---|---|---|
| Calculated for $C_{19}H_{22}N_2O_2$: | 73.52% C | 7.14% H | 9.02% N |
| Found: | 73.57% C | 7.17% H | 8.95% N |

EXAMPLE 35

2,2-Dimethyl-N-[2-(1-acetyl-2,3-dihydro-1H-indol-2-yl)phenyl]propanamide

To an ice cold solution of 3.5 g 2,2-dimethyl-N-[2-(2,3-dihydro-1H-indol-2-yl)phenyl]propanamide in 35 ml $CH_2Cl_2$ was added 8.4 ml triethylamine, followed by dropwise addition of 4.2 ml acetic anhydride. The resulting solution was stirred at room temperature for two hours and then quenched with water. The organic layer was washed successively with 5% aq. HCl, water, saturated $NaHCO_3$ and brine, and dried ($MgSO_4$). Concentration, trituration with hexane and recrystallization from toluene/hexane gave 3.1 g solid, m.p. 184°–186° C.

| ANALYSIS: | | | |
|---|---|---|---|
| Calculated for $C_{21}H_{24}N_2O_2$: | 74.97% C | 7.19% H | 8.33% N |
| Found: | 74.92% C | 7.17% H | 8.24% N |

EXAMPLE 36

2,2-Dimethyl-N-[2-(1-acetyl-2,3-dihydro-1H-indol-2-yl)-4-chlorophenyl]propanamide To a solution of 3.38 g 2,2-dimethyl-N-[2-(2,3-dihydro-1H-indol-2-yl)-4-chlorophenyl]propanamide in 40 ml $CH_2Cl_2$ at 10° C. were added 12.7 ml $Et_3N$ and then dropwise 6.59 ml acetic anhydride. The resulting mixture was stirred twenty-four hours at room temperature. The reaction was quenched with water (30 ml). The organic phase was separated, washed with 5% HCl, water, 7.5% $NaHCO_3$ and sat. NaCl (1×), and dried ($MgSO_4$). Concentration, trituration with hexane and recrystallization from cyclohexane gave 2.10 g solid, m.p. 131°–134° C.

| ANALYSIS: | | | |
|---|---|---|---|
| Calculated for $C_{21}H_{23}ClN_2O_2$: | 68.01% C | 6.25% H | 7.55% C |
| Found: | 68.28% C | 6.40% H | 7.46% N |

EXAMPLE 37

2,2-Dimethyl-N-[2-[2,3-dihydro-1-(ethoxycarbonyl)methyl-1H-indol-2-yl]phenyl]propanamide Ethyl bromoacetate (4.4 ml) was added to a mixture of 3.4 g 2,2-dimethyl-N-[2,3-dihydro-1H-indol-2-yl)phenyl]propanamide and 11.0 g $K_2CO_3$ in 35 ml anhydrous DMF and this was stirred at room temperature for twenty-four hours. The resulting mixture was poured into excess water and the precipitated solid was collected, washed with water and hexane, and air dried to give 3.2 g solid. Recrystallization from cyclohexane gave 1.9 g solid, m.p. 151°–154° C.

| ANALYSIS: | | | |
|---|---|---|---|
| Calculated for $C_{23}H_{28}N_2O_3$: | 72.60% C | 7.42% H | 7.36% N |
| Found: | 72.64% C | 7.40% H | 7.41% N |

EXAMPLE 38

2,2-Dimethyl-N-[4-chloro-2-[2,3-dihydro-1-(ethoxycarbonyl)methyl-1H-indol-2-yl]phenyl]propanamide Ethyl bromoacetate (3.47 ml) was added to a mixture of 2.0 g 2,2-dimethyl-N-[4-chloro-2-(2,3-dihydro-1H-indol-2-yl)-phenyl]propanamide, 5.8 g $K_2CO_3$, and 2.1 ml diisopropylethylamine in 20 ml anhydrous DMF, and this was stirred at room temperature for three days. The resulting mixture was poured into excess water, and the precipitated solid was extracted into $CH_2Cl_2$ and washed with 5% HCl (2×), water (2×) and saturated NaCl (1×), and dried ($MgSO_4$). Concentration and trituration with hexane gave 0.90 g solid. A similar procedure using 4.0 g 2,2-dimethyl-N-[4-chloro-2-(2,3-dihydro-1H-indol-2-yl)phenyl]propanamide yielded 1.49 g solid. The solids from the two experiments were flash chromatographed using 2.5% $Et_2O$/toluene to yield 1.87 g solid, m.p. 177°–179° C.

| ANALYSIS: | | | |
|---|---|---|---|
| Calculated for $C_{23}H_{27}ClN_2O_3$: | 66.58% C | 6.56% H | 6.75% N |
| Found: | 66.72% C | 6.50% H | 6.76% N |

EXAMPLE 39

1-Methoxycarbonyl-2-[2-(methoxycarbonyl)aminophenyl]-2,3-dihydro-1H-indole

Methyl chloroformate (3.80 ml) was added dropwise to a solution of 10.34 g 2-(2-aminophenyl)-2,3-dihydro-1H-indole and 8.40 ml pyridine in 190 ml $CH_2Cl_2$ at 0° C. The solution was stirred five and a half hours at 0° C. and then quenched with water (170 ml). The organic layer was separated, washed with 5% HCl and saturated NaCl solution, dried ($MgSO_4$), and concentrated to yield 7.92 g solid. A similar procedure using 3.00 g 2-(2-aminophenyl)-2,3-dihydro-1H-indole yielded 1.67 g solid. The solids from the two reactions were combined and purified by HPLC. Recrystallization from MeOH/water yielded 2.10 g solid, m.p. 153°–155° C.

| ANALYSIS: | | | |
|---|---|---|---|
| Calculated for $C_{18}H_{18}N_2O_4$: | 66.25% C | 5.56% H | 8.58% N |
| Found: | 66.00% C | 5.37% H | 8.49% N |

EXAMPLE 40

1-(1,1-Dimethylethoxycarbonyl)-2-[2-(1,1-dimethylethoxycarbonyl)aminophenyl]-2,3-dihydro-1H-indole To a mixture of 5.00 g 2-(2-aminophenyl)-2,3-dihydro-1H-indole in 110 ml $CH_2Cl_2$ and 5 ml $Et_3N$ at 10° C. was added 8.83 g di-tert-butyl dicarbonate. The resulting solution was stirred three days at room temperature. It was then washed with 5% NaOH, water and sat. NaCl solution and dried (MgSO₄). Concentration and purification by HPLC using 10% hexane/CH₂Cl₂ yielded a solid. Recrystallization from ethanol/water yielded 2.98 g solid, m.p. 148°-150° C.

ANALYSIS:

| | | | |
|---|---|---|---|
| Calculated for $C_{24}H_{30}N_2O_4$: | 70.22% C | 7.37% H | 6.82% N |
| Found: | 70.01% C | 7.29% H | 6.71% N |

EXAMPLE 41

(4-Amino-6-phenylamino-3-pyridyl)carbonitrile

4-Amino-3-cyano-1,2,5,6-tetrahydropyridine (15.0 g) was dissolved in 300 ml nitrobenzene containing 5.0 g 5% Pd on alumina and 0.19 ml acetic acid. The reaction mixture was heated to 170° C. and the pressure adjusted to approximately 230 mmHg, and maintained under these conditions for two hours. Water formed during the reaction was separated by nitrogen sweep. The reaction mixture was filtered through celite at 100° C. and the resultant solution cooled and diluted with pentane to precipitate a solid. This solid was collected and dried. Purification by HPLC using 2% CH₃OH/CH₂Cl₂ yielded 1.75 g solid, m.p. 209°-211° C.

ANALYSIS:

| | | | |
|---|---|---|---|
| Calculated for $C_{12}H_{10}N_4$: | 68.56% C | 4.79% H | 26.65% N |
| Found: | 68.11% C | 4.83% H | 26.48% N |

We claim:

1. A compound having the formula

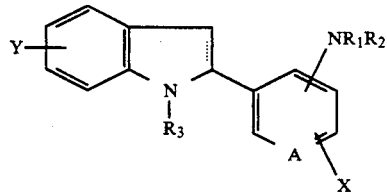

where
A is N;
X is hydrogen, loweralkyl, halogen, trifluoromethyl, loweralkoxy, arylloweralkoxy, hydroxy or phenylamino;
Y is hydrogen, loweralkyl, halogen, loweralkoxy, arylloweralkoxy or hydroxy;
R₁ is hydrogen or loweralkyl;
R₂ is hydrogen, loweralkyl, formyl, alkylcarbonyl, arylloweralkylcarbonyl, arylcarbonyl, alkoxycarbonyl, arylloweralkoxycarbonyl or aryloxycarbonyl; and
R₃ is hydrogen, alkyl, alkylcarbonyl, arylloweralkylcarbonyl, arylcarbonyl, alkoxycarbonyl, arylloweralkoxycarbonyl, aryloxycarbonyl or —CH₂CO₂C₂H₅;
the term aryl in each occurrence signifying a phenyl group optionally mono-substituted with a loweralkyl, loweralkoxy, halogen or trifluoromethyl group or a pharmaceutically acceptable acid addition salt thereof.

2. The compound as defined in claim 1, wherein the fused ring system is an indole ring.
3. The compound as defined in claim 1, wherein the fused ring system is a 2,3-dihydro-1H-indole ring.
4. The compound as defined in claim 1, which is 2-(4-amino-3-pyridinyl)-1H-indole.
5. The compound as defined in claim 1, which is 2-[4-(octyloxycarbonyl)amino-3-pyridinyl]-1H-indole.
6. The compound as defined in claim 1, which is 2-(4-amino-3-pyridinyl)-2,3-dihydro-1H-indole.
7. The compound as defined in claim 1, which is 2-(2-amino-3-pyridinyl)-2,3-dihydro-1H-indole.
8. A pharmaceutical composition comprising a compound as defined in claim 1 in an amount effective for treating an inflammatory skin disorder and a suitable carrier therefor.
9. A method of treating a patient in need of relief from an inflammatory skin disorder which comprises administering to such a patient an effective amount of a compound as defined in claim 1.

* * * * *